United States Patent [19]

Kirsch

[11] Plant 4,085

[45] July 26, 1977

[54] LILY PLANT NAMED STAR GAZER

[76] Inventor: Ted T. Kirsch, Sitkum Rte. Box 142, Myrtle Point, Oreg. 97458

[21] Appl. No.: 726,481

[22] Filed: Sept. 24, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct variety of lily plant of the Parkman type of Oriental hybrid, particularly distinguished by its large, upwardly facing, bright red flowers borne on sturdy pedicels which curve outwardly and upwardly from a strong upright stem to terminate with the flower axis substantially vertical, the flowers being bowl-shaped with white margins bordering its red sepals and petals and an excellent lasting quality both on the stem and as a cut flower.

1 Drawing Figure

BACKGROUND OF THE NEW PLANT

My new variety of lily plant originated as a seedling of unknown parentage and was discovered by me in 1971 among plants grown in a test plot maintained by me at Arcata, Calif., in connection with my endeavors to develop new and improved lily varieties. The very unusual upwardly facing presentation of the flowers of this plant and the beautiful almost solid red coloration of the flowers determined it to be a new variety quite different than any other Parkman Oriental lily and my subsequent vegetative propagation of this plant, through successive generations at Arcata, Calif., has demonstrated that its distinctive characteristics hold true from generation to generation and appear to be firmly fixed. As a result, this new lily variety is now being propagated on a commercial scale at Arcata, Calif., by means of scales and tissue culture.

DESCRIPTION OF THE DRAWINGS

This new variety of lily plant is illustrated by the accompanying photographic drawings which, in full color, show a full face view of several flowers made from directly above a vertical stem, a view of the plant at about midway of its blooming cycle, and a view of the plant just before the blooming of its first flower, the color rendition being as nearly true as it is reasonably possible to be had through conventional photographic procedures.

DESCRIPTION OF THE NEW PLANT

The following is a detailed description of my new variety of lily plant with the color designation being according to the R.H.S. Colour Chart published by The Royal Horticultural Society of London, England, the observations being made of greenhouse plants at Arcata, Calif., in the summer of 1976, unless otherwise indicated.

THE PLANT

Origin: Seedling.

Parentage: Unknown.

Classification: Oriental Hybrid. Parkman.

Form: Tall single stem from each bulb.

Height: Two to 4 feet depending upon age of bulb.

Growth: Sturdy and upright with excellent strength.

*Stem size.*—From about ⅜ inch diameter at base of 2 foot stem to 1 inch diameter for plants reaching a height of about 4 feet.

Foliage: Abundant in quantity.

*Size of leaves.*—Stem leaves are from 3 to 4 inches long and from 1½ to 2 inches wide. In the axil of the inflorescence the leaves are usually larger than the stem leaves. Directly under the pedicel the leaves angle outwardly and then sideways except at the very top buds the leaves go directly outward from the pedicel.

*Shape of leaf.*—Lanceolate.

*Texture.*—Leathery.

*Aspect.*—Smooth.

*Ribs and veins.*—Distinct longitudinal veins from base to tip.

Bulblets (stem): Occurrence — from one to six at digging time.

*Size.*—From ¼ inch to 1 inch in diameter.

*Color.*—White, with occasional pink shading at the tips.

Bulbs: Blooming size — 1 inch in diameter and larger.

*Color.*—White with yellow and pink overtones. As bulbs become larger and older the overtones of yellow and pink become more and more prominent.

THE BUD

Form: Elongate with obtuse apex.

Size: 3 to 5 inches long and ¾ to 1½ inches in diameter.

Number: Usually only one on each pedicel, with 1 to 15 buds on a plant according to culture and bulb size.

Opening: Normal, buds open successively from the lowermost bud to the top bud which is the last to open.

Color: Changing from dark green to reddish brown overtones, then to pink with a white tip just before the sepals divide and the petals begin to unfurl, and finally turning red with a white margin when fully opened.

Pedicel: Strong and stiff, the lower pedicels curving outwardly and upward to present the bulb and blossom vertically. At the top of the stem the pedicels rise vertically.

*Length.*—3½ to 4½ inches.

THE FLOWER

Blooming habit: Annually. Blooming profusely in August.

Size: Large, averaging $6\frac{1}{2}$ to $7\frac{1}{2}$ inches in diameter.

Shape: Generally flat with a slight bowl form with petals turning slightly downward at the tips. The sepals and petals are uniformly spaced in a star arrangement.

Petalage: Normal. Three sepals and three petals.

*Form.*—Elliptical with an obtuse apex, with prominent nectariferous grooves and a center furrow longitudinally bisecting each petal.

Papillae: Very apparent and extending on each side of the rectory approximately $\frac{3}{8}$ inch long at the beginning and decreasing to $\frac{1}{8}$ inch in length as bloom matures.

*Color.*—White with pink tip.

Texture: Leathery.

Aspect: Velvety.

Color:

*Upper side.*—When fully opened, the sepals and petals are red 64B in the central portion changing to 64D approaching the margins which have a distinct white edge about $\frac{1}{8}$ inch wide. The nectariferous groove is green and about $1\frac{1}{2}$ inches long extending to the base portion of the petal. Numerous oblong raised spots of a very dark red color are to be found extending from the papillae for about three-quarters of the length of each petal and sepal.

*Under side.*—When the blossom first opens, there is a whitish-light pink cast and as the flower matures, the petals become darker and the white is confined to the margins and darker or reddish pink is more overall with a center rib or vein which is redder than the overall color. As the flower matures, the color becomes darker giving it a bluish cast at the end of the senescence.

Fragrance: Spicy.

Effect of weather: Generally weather has no effect on the flower, but the flower ages more quickly as temperature rises. In the field or garden a cool climate will produce a darker color while heat tends to lighten the flower color.

Persistence: The flower tends to hang on and dry.

Lasting quality:

*On the plant.*—2 to 3 weeks depending on the size of the bulb and environmental temperature.

*As cut flower.*—10 days to 2 weeks.

REPRODUCTIVE ORGANS

Stamens: Number — 6.

*Arrangement.*—Orderly around the pistil.

*Anthers.*—Length — about 1 inch.

*Filaments.*—Length — about 2 inches. Color: Greenish yellow.

Pistil: Number — one.

*Style.*—Length — about $3\frac{1}{2}$ inches.

*Stigma.*—Color — brown.

Ovary: Contained in a seed pod about 2 inches long and $1\frac{1}{4}$ inches in diameter and having 6 rows of seeds of the usual shape for lilies.

This new variety of Parkman Oriental lily plant is most unique in that it is the first known commercial lily in this class to bloom facing directly upward. Lilies in this class have blossoms facing either outward or downward.

Plants of this new variety when grown in the open, in field or garden, have a purplish red bud before opening and are completely red in color when first opened. The flowers remain more bowl shaped than when grown in the greenhouse, the color is a deeper red and there is no white marginal edging of the petals and sepals. The flowers are not as large and when cut in the bud the flowers flatten down, the petals curl under much more and a thin white marginal border begins to appear only as the flowers unfold up the stem becoming somewhat wider near the petal tips. This white border is not, however, as wide as on the flowers of greenhouse grown plants.

It is also characteristic of this new lily variety that the shade of the red coloring of the flowers becomes somewhat lighter as the buds open successively, from the first flower to the last, the darker shades being in the lower flowers.

I claim:

1. A new and distinct variety of Oriental hybrid lily plant substantially as herein shown and described, characterized by its very large upwardly facing flowers borne on strong, stiff vertically projecting pedicels, by the substantially overall bright red coloring of the sepals and petals which are bordered by a marginal band of white, and by the long lasting quality of the blooms whether on the plant or as cut flowers.

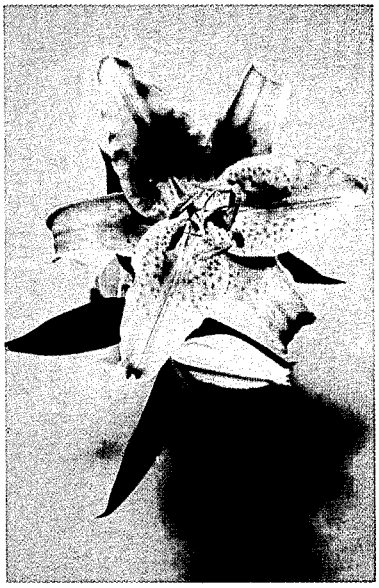
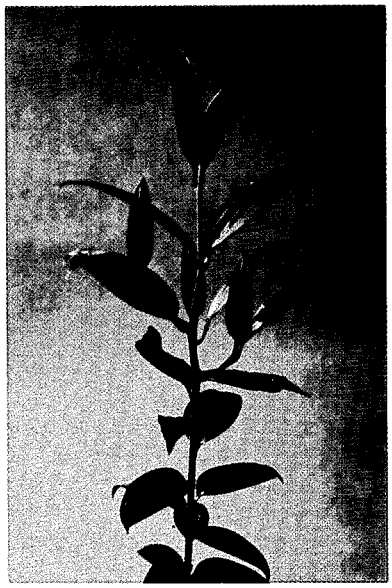
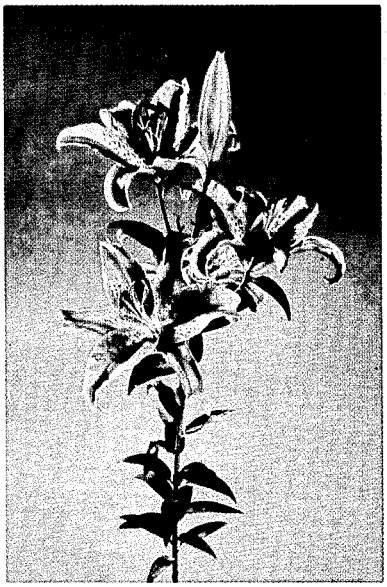

* * * * *